US012396646B2

(12) United States Patent
Huber et al.

(10) Patent No.: US 12,396,646 B2
(45) Date of Patent: Aug. 26, 2025

(54) DEVICE AND METHOD FOR MEASURING TISSUE TEMPERATURE (71) Applicant: Aesculap AG, Tuttlingen (DE)

(72) Inventors: Christian Huber, Muehlheim (DE); Christoph Rothweiler, Donaueschingen (DE); Detlef Russ, Renningen (DE); Oliver Fugger, Ulm (DE); Raimund Hibst, Erbach (DE)

(73) Assignee: Aesculap AG, Tuttlingen (DE)

( * ) Notice: Subject to any disclaimer, the term of this patent is extended or adjusted under 35 U.S.C. 154(b) by 797 days.

(21) Appl. No.: 17/632,899

(22) PCT Filed: Aug. 5, 2020

(86) PCT No.: PCT/EP2020/072027
§ 371 (c)(1),
(2) Date: Feb. 4, 2022

(87) PCT Pub. No.: WO2021/023780
PCT Pub. Date: Feb. 11, 2021

(65) Prior Publication Data
US 2022/0313093 A1    Oct. 6, 2022

(30) Foreign Application Priority Data
Aug. 7, 2019   (DE) .................. 10 2019 121 366.5

(51) Int. Cl.
*A61B 5/00*      (2006.01)
*A61B 5/01*      (2006.01)
(Continued)

(52) U.S. Cl.
CPC .......... *A61B 5/0075* (2013.01); *A61B 5/0084* (2013.01); *A61B 5/01* (2013.01);
(Continued)

(58) Field of Classification Search
CPC .................. A61B 5/0075; A61B 5/01; A61B 2017/00057; A61B 2018/00601;
(Continued)

(56) References Cited

U.S. PATENT DOCUMENTS

| 5,348,396 A | 9/1994 | O'Rourke et al. |
| 7,976,537 B2 | 7/2011 | Lieber et al. |

(Continued)

FOREIGN PATENT DOCUMENTS

| CN | 101199410 A | 6/2008 |
| CN | 101332083 A | 12/2008 |

(Continued)

OTHER PUBLICATIONS

Search Report received in German Application No. 10 2019 121 366.5 dated Jun. 9, 2020, with translation, 13 pages.

(Continued)

*Primary Examiner* — Eric F Winakur
*Assistant Examiner* — Noah M Healy
(74) *Attorney, Agent, or Firm* — Christopher A. Rothe; CM Law (57) ABSTRACT

A device and a method for measuring temperature. At least one illumination device emits light with an illumination spectrum into tissue. At least one detector receives the diffuse reflection of the light with a remission spectrum from the tissue. The detector converts the remission spectrum into a detector signal. The detector signal is sent to a computing unit that calculates a remission spectrum from the detector signal. The computing unit calculates an absorption spectrum of the tissue by comparing the illumination spectrum with the remission spectrum, calculates at least one absorption maximum from the absorption spectrum, and calculates a temperature in the tissue by comparing the absorption maximum with at least one reference.

17 Claims, 6 Drawing Sheets (51) Int. Cl.
*A61B 17/00* (2006.01)
*A61B 18/00* (2006.01)

(52) U.S. Cl.
CPC ............... *A61B 2017/00057* (2013.01); *A61B 2018/00601* (2013.01)

(58) Field of Classification Search
CPC .. A61B 2018/00607; A61B 2018/0063; A61B 2018/00797; A61B 18/12; A61B 18/14; A61B 2018/00791
See application file for complete search history.

(56) References Cited

U.S. PATENT DOCUMENTS

| | | |
|---|---|---|
| 8,426,819 B2 | 4/2013 | Herrmann |
| 9,554,708 B2 | 1/2017 | Lee |
| 2005/0288654 A1 | 12/2005 | Nieman et al. |
| 2011/0077547 A1 | 3/2011 | Baker, Jr. |
| 2011/0251605 A1 | 10/2011 | Hoarau et al. |
| 2013/0131671 A1 | 5/2013 | Baker, Jr. |
| 2015/0209105 A1 | 7/2015 | Margallo Balbas et al. |
| 2015/0289767 A1 | 10/2015 | Keller et al. |
| 2016/0089198 A1 | 3/2016 | Arya et al. |
| 2016/0346034 A1 | 12/2016 | Arya et al. |
| 2017/0238991 A1 | 8/2017 | Worrell et al. |

FOREIGN PATENT DOCUMENTS

| | | |
|---|---|---|
| CN | 103907001 A | 7/2014 |
| JP | H11183377 A | 7/1999 |
| JP | 2007271399 A | 10/2007 |
| JP | 2008501441 A | 1/2008 |
| JP | 2011510312 A | 3/2011 |
| WO | 2012120498 A1 | 9/2012 |
| WO | 2016196196 A1 | 12/2016 |

OTHER PUBLICATIONS

Search Report received in International Application No. PCT/EP2020/072027 dated Nov. 5, 2020, with translation, 8 pages.
Written Opinion received in International Application No. PCT/EP2020/072027 dated Nov. 5, 2020, with translation, 15 pages.
Office Action received Japanese Application No. 2022-507542 dated Apr. 26, 2024, with translation, 14 pages.
Communication received in European Application No. 20 753 713.5-1113 dated Nov. 29, 2024, with translation, 10 pages.
Notice of Allowance received in Japanese Application No. 2022-507542 dated Nov. 12, 2024, with translation, 2 pages.
Office Action received in Chinese Application No. 202080056162.0 dated Jan. 26, 2025, with translation, 39 pages.

DEVICE AND METHOD FOR MEASURING TISSUE TEMPERATURE

CROSS-REFERENCES TO RELATED APPLICATIONS

This application is the United States national stage entry of International Application No. PCT/EP2020/072027, filed Aug. 5, 2020, and claims priority to German Application No. 10 2019 121 366.5, filed Aug. 7, 2019. The contents of International Application No. PCT/EP2020/072027 and German Application No. 10 2019 121 366.5 are incorporated by reference herein in their entireties.

FIELD

The invention relates to a device and a method for measuring tissue temperature in particular of human tissue in a medical high-frequency surgical instrument during a thermal process (HF, ultrasonic, laser instrument, etc.).

BACKGROUND

In high-frequency surgery (hereinafter referred to as HF surgery), high-frequency alternating current is passed through the human body or a body part to specifically obliterate (coagulation) or cut (electrotomy) tissue by the heating caused in this way. The tissue damaged in this way is resorbed later by the surrounding normal tissue. A substantial advantage over the conventional cutting technique by a scalpel resides in the fact that hemorrhage can be stopped simultaneously with the cut by sealing the affected vessels in the sense of coagulation. For safely sealing vessels, so-called seal and cut instruments should be used. The devices used are also referred to as electrotomes.

At the frequencies used for HF surgery (high-frequency surgery), the body tissue behaves like an ohmic resistance (impedance). The resistivity is strongly dependent on the type of tissue. The resistivity of muscle tissue and strongly perfused tissue is relatively low. The resistivity of fat is higher by about the factor 15 and that of bone is higher by the factor 1000. Hence, the frequency, the form and the intensity of current must/should be adapted to the type of tissue which is operated on.

Currently, the monopolar HF technique is used most frequently in HF surgery. Accordingly, one pole of the HF voltage source is connected to the patient via counter-electrode with as large an area as possible, e.g., by contacts on the operating table on which the patient is placed by contact bracelets or contact anklets or by adhesive electrodes. Said counter-electrode is frequently referred to as neutral electrode. The other pole is connected to the surgical instrument which then forms the so-called active electrode. The current flows via the path of lowest resistance from the active electrode to the neutral electrode. In the direct vicinity of the active electrode, there current density is highest and here the strongest thermal effect occurs. The current density decreases with the square of the distance. The neutral electrode should have as large an area as possible and should be properly connected to the body so that the current density in the body is kept low and no burns will occur. The skin at the neutral electrode is not noticeably heated due to the large surface. Strict safety measures are applicable when attaching the neutral electrode. The correct position and the proper contact of the neutral electrode (depending on the operating area) are crucial so that no burns are caused.

Unlike the monopolar technique, in the bipolar HF technique the current flows through a small part of the body—the part where the surgical effect (cut or coagulation) is desired. Two electrodes insulated from each other (e.g., received in instrument branches) between which the HF voltage is applied are guided directly to the operating site. The electric circuit is closed via the tissue located therebetween. The thermal effect takes place in the tissue between the electrodes.

Coagulation clamps are known. The high-frequency terminals are usually provided at the handles/handle. The axis for the joint frequently is a screw provided with an insulating coating by which screw also the two clamping legs with their handles are pivotably secured to each other.

Vessels or tissue bundles can be efficiently and permanently sealed by a bipolar HF tissue sealing and/or cutting system allows in general or during cutting. Thus, the lateral thermal damage of the surrounding tissue is limited, and tissue adhesions are minimized.

In medicine, tissue is an organic material consisting of a group of similarly or differently differentiated cells which have a joint function or structure. The tissue also includes, apart from the cells, the extracellular matrix (ECM). Examples of human tissues are blood vessels, for example.

The chemical composition of the human body consists of about 56% oxygen (O), 28% carbon (C), 9% hydrogen (H), 2% nitrogen (N), 1.5% calcium, 1% chlorine (Cl), 1% phosphorus (P), 0.25% potassium (K), 0.2% sulfur (S) and other chemical substances in smaller contents (all indications in percent by weight).

The substance composition of the human body consists of about 67% water, 16% proteins or albumin (such as collagens), 10% lipids (such as fat), 1% hydrocarbons, 1% nucleic acids and 5% diverse minerals (all indications in percent by weight).

Collagens are a group of structural proteins (an "albumin" forming fiber bundles) mainly of the connective tissue (more precisely: of the extracellular matrix) which occur in human beings and animals. Collagens are found, inter alia, in the white non-elastic fibers of tendons, ligaments, bones and cartilages. Layers of the skin (subcutis) also consist of collagens. In the human body, collagen is the most frequently occurring albumin with a content of more than 30% in the total mass of all proteins.

In living organisms, lipids are primarily used as structural components in cell membranes, as energy storages or as signal molecules. The term "fat" is often used as a synonym for lipids, but the fats (triglycerides) are only a sub-group of the lipids.

Optical main absorbers in tissue such as in blood vessels in the NIR region are water and collagen. The blood vessels are usually surrounded by fat.

When electromagnetic radiation interacts with sold bodies, liquids or gases, different effects such as absorption, reflection, dispersion or transmission occur. In other words, when the electromagnetic radiation impacts an obstacle, it is either absorbed (swallowed), dispersed (deflected from its original direction), transmitted (allowed to pass) or reflected (thrown back)—the reflection is also referred to as diffuse reflection.

In physics, diffuse reflection is the diffuse (non-directed) electromagnetic radiation, in particular of light, which penetrates a scattering medium through the surface, interacts with the same and exits through said surface again. This is in contrast to the regular directed reflection that fulfills the law of reflection. More frequently, in both cases it is called reflection, however. Then a distinction is made between specular reflection and diffuse reflection. In the diffuse reflection, part of the light is absorbed and transmitted. The surface-related measure for the diffuse reflection is the degree of diffuse reflection.

The diffuse reflection spectroscopy is a sub-field of spectroscopy that measures the radiation remitted by a specimen. The diffuse reflection spectroscopy mainly serves for spectral examination of opaque and non-soluble specimen. The measured diffuse reflection spectrum of a specimen consists of two parts: 1) the regular reflection in which the radiation is specularly reflected by the surface. It is described by the Fresnel equations; 2) the diffuse reflection in which the radiation exits the specimen in an isotropic manner in all directions. It is formed by the fact that the radiation penetrates the specimen and after partial absorption and multiple dispersion returns to the surface.

The respective absorption spectrum of water, collagen and fat has been measured by numerous groups. Both in the visible spectral range (VIS) and in the near infrared spectral range (NIR), the values for the absorption coefficients are available.

In prior art, the control processes in bipolar HF technique are controlled via the tissue impedance which changes in the course of the energy supply, primarily by the loss of water. The impedance of the tissue is calculated using the ohmic law by means of the measured voltage and current values. Due to the configuration of an instrument, the established impedance always is an average value of the entire system (tissue, instrument, cable, generator).

The quality of the sealing of blood vessels is substantially dependent on the control process and the related input of energy into the tissue. Apart from overheating of the instruments, also thermal damage of the surrounding tissue may occur in this context. Equally, insufficient energy input may also result in the failure/bursting of the fused sites, which in turn becomes noticeable by hemorrhages. Such hemorrhages frequently occur as late as several hours after the actual operation so that, depending on the vessel diameter, emergency operations may become necessary to stop the hemorrhage and to safely seal the vessel.

Therefore, it is known from prior art to measure the tissue temperature and to incorporate the measured temperature values in the regulation/control of the thermal process. To prevent the temperature measuring results from being falsified by the electrode temperature, a sufficiently large distance or a thermal separation/insulation between the tissue temperature sensor and the electrode(s) is required. This is a drawback, however, insofar as the measured tissue temperature does not exactly correspond to the tissue temperature directly at the electrode(s).

SUMMARY

It is therefore the object of the invention to enable, in addition or as an alternative to the measurement of the impedance, the temperature of the tissue to be fused to be measured as precisely as possible, preferably online, to carry out a controlled energy input (electrical and thermal) or a controlled reversible "damage" of the tissue directly at the electrode(s) and, where necessary, also to prevent the instruments from overheating. In other words, it is the object of the invention to allow for safe sealing of the fused vessels by the additional monitoring of the temperature in the tissue.

The invention relates to a method for measuring temperature, preferably in a medical instrument, particularly preferred during a thermal method/process, comprising the steps (preferably in the following order):

emitting light with an illumination spectrum, preferably in the VIS/NIR range, into tissue by at least one illumination device and/or a plurality of illumination devices, receiving the diffuse reflection of the light with a diffuse reflection spectrum from the tissue by at least one detector, preferably a sensor, and/or a plurality of detectors, wherein the plurality of illumination devices and the plurality of detectors are formed or arranged in or on at least one instrument branch or alternately on two opposite instrument branches and are in electric connection with a computing unit, converting the diffuse reflection spectrum into a detector signal, preferably an electrical signal/data signal by means of the detector and/or the detectors, sending the detector signal to the computing unit, preferably a CPU, evaluating the diffuse reflection spectrum from the detector signal by means of the computing unit, evaluating an absorption spectrum of the tissue by comparing the illumination spectrum to the diffuse reflection spectrum by means of the computing unit, determining at least one absorption maximum from the absorption spectrum by means of the computing unit, and calculating a temperature in the tissue by comparing the absorption maximum to at least one reference, which is preferably stored in the computing unit, by means of the computing unit.

A plurality of detectors is formed or arranged, according to the foregoing aspect, alternately on two opposite instrument branches and is electrically connected to a computing unit. In other words, this means that each of an illumination device and a detector are alternately arranged on an instrument branch, wherein on the opposite instrument branch an illumination device is opposed to the illumination device and a detector is opposed to the detector to reduce or avoid falsification of measurement at the respective detector by light input on the opposite side.

Preferably, a thermal process is any process that generates thermal effects in the tissue by energy output. These include also processes carried out by high frequency, ultrasound, laser and/or temperature. Also, processes are included that are carried out by high-frequency, ultrasonic, laser and/or temperature instruments (such as by thermocautery), and/or all medical instruments which generate thermal effects in the tissue by energy output.

Consequently, the core of the present invention resides in the fact that the (tissue) temperature is not directly measured but is determined by measuring a different parameter (unlike the temperature) which, on the one hand, allows to directly or indirectly conclude the current temperature (causal relationship between the temperature and the parameter) and, on the other hand, is (exclusively) specific to the tissue, i.e., is not influenced by the electrode(s). The tissue temperature is established by means of the position/course of at least one absorption maximum/absorption maximum spectrum/absorption maximum range. This means that the absorption maximum may be a (numerical) single value, a plurality of values, a range or a spectrum, wherein hereinafter only the term absorption maximum shall be used as the principle remains the same. More precisely, at least one absorption spectrum/absorption spectrum range/absorption energy proportion (qualitative proposition) of the tissue is established, preferably for at least one tissue component, by putting the diffuse reflection spectrum in relation to the illumination spectrum, preferably dividing them. The illumination spectrum is the spectrum emitted by the light source of the illumination device, and the diffuse reflection spectrum is the spectrum remitted by the tissue. Preferred tissue components are water, fat and/or collagen. It can be established from the absorption spectrum obtained in this way at which position at least one absorption maximum of the absorption spectrum of the tissue, preferably of at least one tissue component, is provided. The absorption maximum or the absorption maximum range, preferably the wavelength, the frequency of the wavelength, the wave number or the position of the absorption maximum, is compared to at least one reference stored in the computing unit, preferably in the storage medium. The at least one stored reference then can be established from a table or by reference measurement so that it can be found that a particular temperature is prevailing in the tissue at a particular position/wavelength/frequency/wave number of the absorption maximum. Unless said position/wavelength/frequency/wave number of the absorption maximum is stored in a table, the temperature in the tissue can be calculated by shifting the calculated position/wavelength/frequency/wave number of the absorption maximum from a deposited position/wavelength/frequency/wave number of the absorption maximum on the computing unit. Instead of the absorption maximum, also any other position/wavelength/frequency/wave number from the absorption spectrum which has a significant recognition value (such as maximums or minimums) can be used.

The tissue proportions of the tissue have a typical absorption characteristic. Water, for example, has an absorption maximum at about 1470 nm at room temperature, collagen, on the other hand, has an absorption maximum at about 1500 nm at room temperature, and fat has an absorption maximum at each of 1210 nm and about 1400 nm at room temperature. Preferably, the absorption maximum of water at 1470 nm is +/−20 nm, especially preferred at 1470 nm is +/−10 nm, particularly preferred at 1470 nm is +/−5 nm. Preferably, the absorption maximum of collagen at 1500 nm is +/−20 nm, particularly preferred at 1500 nm is +/−10 nm, particularly preferred at 1500 nm is +/−5 nm. Preferably, the absorption maximum of fat at 1210 and at 1400 nm is +/−20 nm, particularly preferred at 1210 and at 1400 nm is +/−10 nm, particularly preferred at 1210 and at 1400 nm is +/−5 nm.

The method preferably comprises the further step of:
storing at least one reference in the form of an absorption maximum at a particular temperature in the computing unit, preferably a storage medium in the computing unit, preferably for water and/or fat and/or collagen.

Preferably, by means of the computing unit based on the characteristic absorption spectrum of water as reference, it can be established which temperature is prevailing in the tissue. The fact that water at a particular temperature has a particular absorption maximum (e.g., 1470 nm at room temperature) is stored in the computing unit or the storage medium. By comparing the shift of the absorption maximums from a pre-stored value and/or comparing to a plurality of predetermined corresponding values in a stored table, it can be established at which wavelength of the absorption maximum which temperature is prevailing in the water of the tissue. The characteristic absorption spectrum of water is simplest to determine, as the tissue components in the body are known and water with about 67% has the largest content in the tissue. Due to the measured absorption spectrum, the shift of the spectral absorption maximum of water can be calculated/established. The temperature can be determined based on said shift of the absorption maximum which is about 0.5 nm/K. The foregoing can be applied analogously to fat and/or collagen and/or other components of the tissue.

The above steps for measuring the absorption spectrum can be applied analogously, apart from water, also to fat, collagen or other tissue components. Thus, the individual absorption spectrums of water, fat and collagen in tissue can be established from an absorption spectrum which is detected by a detector and is established by a computing unit.

Preferably, the method comprises the further step of:
applying the illumination device and the detector to the tissue.

Advantageously, the detector and the illumination device are thus in direct contact with the tissue.

Preferably, the method comprises the further step of:
controlling and/or regulating and/or switching off a device, preferably a medical instrument, by means of the computing unit based on the calculated temperature and/or tissue impedance.

Controlling and/or regulating and/or switching off preferably takes place when a predetermined temperature is reached, preferably a temperature of more than 85° C. and less than 110° C., particularly preferred a temperature of more than 95° C. and less than 100° C. The coagulation of tissue achieves the best result at a temperature, preferably a constant temperature, of more than 85° C. and less than 110° C., particularly preferred at a temperature of more than 95° C. and less than 100° C.

Preferably, all steps are carried out online/real-time. This means that controlling and/or regulating and/or switching off the medical instrument is/are carried out online, preferably real-time. In other words, the absorption spectrum of the tissue is measured online, preferably real-time, thus allowing the temperature within the tissue to be calculated online, viz. real-time. The temperature is then incorporated preferably online, preferably real-time, in the control/regulation of at least one electrode/sonotrode/laser source of the medical instrument, preferably of the cut and seal device.

Preferably, the method for measuring temperature is carried out during a sealing operation, especially preferred within the tissue in the medical instrument.

Preferably, the detectors are provided and adapted to detect diffuse reflection, preferably the diffuse reflection spectrums, in the NIR range from 1000 nm to 1700 nm, particularly preferred in the range from 1400 nm to 1600 nm.

Preferably, the at least one illumination device and the at least one detector are spaced apart from each other, preferably in a medical instrument.

Preferably, the method for measuring a tissue temperature is applied in a medical instrument.

A temperature measuring device preferably comprises a storage medium in which at least one of the following steps is stored (if there are plural steps, preferably in this order):
storing at least one reference in the form of an absorption maximum at a particular temperature in the computing unit, preferably a storage medium in the computing unit, preferably for water and/or fat and/or collagen,
applying the illumination device and the detector to the tissue.

Advantageously, the detector and the illumination device are thus in direct contact with the tissue.
emitting light with an illumination spectrum, preferably in the VIS/NIR range, into a tissue by means of at least one illumination device,
receiving the diffuse reflection of the light with a diffuse reflection spectrum from the tissue by at least one detector, preferably a sensor, converting the diffuse reflection spectrum by means of the detector into a detector signal, preferably an electrical signal/data signal, sending the detector signal to a computing unit, preferably a CPU, calculating the diffuse reflection spectrum from the detector signal by means of the computing unit, calculating an absorption spectrum of the tissue by comparing the illumination spectrum with the diffuse reflection spectrum by means of the computing unit, calculating at least one absorption maximum from the absorption spectrum by means of the computing unit, calculating a temperature in the tissue by comparing the absorption maximum to at least one reference preferably stored in the computing unit by means of the computing unit, and controlling and/or regulating and/or switching off a device, preferably a medical instrument, by means of the computing unit based on the calculated temperature and/or tissue impedance.

In other words, in temperature measurement, during a sealing operation, diffuse reflection spectrums in the NIR range from 1000 nm to 1700 nm are detected online by a detector. The shift of the position of the absorption maximums which can be derived from the recorded spectrums can be utilized to conclude the temperature of the tissue held in the instrument with an accuracy sufficient for the application. With an increasing temperature, the position of the absorption peak shifts toward shorter wavelengths. The shift is about 0.5 nm/K. When the tissue continues cooling, the absorption peak shifts toward longer wavelengths again. Since the main absorber in the tissue to be sealed in the wavelength range of about 1470 nm is water, the temperature determined in this way reflects the temperature in the water content of the tissue. It is the particular advantage of this temperature measuring method that the actual temperature in the tissue can thus be measured, as, due to the dispersion, the NIR radiation can pass through the entire thickness of the tissue layer. In contrast to that, when measuring the temperature during sealing by a thermocouple, merely the temperature of the contact surface is measured. The temperature and the thermal capacity of the electrodes constitute a disturbance for determining the tissue temperature in this method. Said disturbance results in latency periods and falsifications of the true tissue temperature. Thus, this method does not reflect the tissue temperature but represents the temperature of the surroundings which the thermocouple is in contact with. The optical temperature determination allows to obtain important parameters for the control of the sealing process. Further, the established temperature can be utilized as a switch-off/regulation/control criterion/process parameter or for process regulation/process control.

It has turned out that light of preferably particular wavelength (e.g., white light in the VIS-NIR range) is remitted by the body tissue, wherein the spectrum of the light remitted by the body tissue changes depending on temperature. Hence, it is possible to bring an illumination device/illumination output for radiating body tissue and a detector/detector input for detecting light remitted by the body tissue directly close to the electrode(s) and, thus, to determine the tissue temperature in direct vicinity to (between) the electrode(s) via the bypass of the detected remitted light and the spectral dispersion thereof.

In the preferred embodiment, a medical instrument (of the HF design) therefore includes at least one instrument branch which forms at least one electrode to be supplied with current for sealing and/or cutting tissue or is arranged in or on the at least one electrode to be supplied with current for sealing and/or cutting tissue, wherein the supply of current to the electrode can be controlled and/or regulated by a computing unit, and at least one temperature measuring device comprising at least one illumination device and at least one light detector which is/are formed or arranged (alternately) in or on the at least one instrument branch or in opposite position in/on two instrument branches and which are electrically connected to the computing unit. In other words, on one instrument branch each of an illumination device and a detector are alternately arranged, wherein on the opposite instrument branch an illumination device is opposed to the illumination device and a detector is opposed to the detector.

Preferably, the medical instrument is a surgical instrument, a monopolar instrument, a bipolar instrument, an electrosurgical instrument, a surgical clamp, a surgical clip, surgical forceps, surgical scissors, a scalpel and/or the like. Particularly preferred, the medical instrument is a seal and cut instrument that is provided and adapted to cut and simultaneously seal tissue by means of HF technology. Monopolar instruments offer the advantage that due to their single-shell design (only one single instrument branch) a compact design and, thus, lower manufacturing costs thereof are possible. Bipolar instruments (two opposite instrument branches) offer the advantage that a separate analysis can be better realized and that they are more variable when realizing the replication.

Preferably, the at least one instrument branch is to be understood as the part/end of a medical instrument whose distal part is an instrument branch body or tissue engaging portion (branch body) that can be brought into contact with the tissue, and whose proximal part is in the form of an actuating or handle portion. Further preferred, the at least one instrument branch is a jaw part branch. The instrument branch body of the at least one instrument branch may be in the form of an electrode for sealing tissue, preferably the instrument branch body is made of one piece/of one single part of a conductive metal or graphite. As an alternative, the electrode may be formed/disposed/embedded in and/or at and/or on the instrument branch, in this case the instrument branch is preferably made of an insulator or an electrically insulating material.

Preferably, the medical instrument comprises two opposite instrument branches which are preferably movable/pivotable against each other and at the end of which sides/jaws/portions/instrument branch ends/instrument branch bodies facing each other are arranged/formed which can be brought into contact with the tissue. The instrument branch ends/instrument branch bodies can themselves be in the form of electrodes for sealing tissue, preferably the instrument branch ends/instrument branch bodies are made of conductive metal or graphite and are insulated from each other. However, the electrodes may also be formed/arranged/embedded in and/or at and/or on the instrument branch ends/instrument branch bodies, preferably the instrument branches are made of an insulator or an electrically insulating material or are made of metal and insulated from the electrodes.

Preferably, at least one electrode can be controlled and/or regulated by the computing unit. More precisely, the current intensity, the voltage, the phase and/or the frequency of the electric current applied to the electrode can be controlled or regulated.

Preferably, the temperature measuring device is an optical temperature measuring device/a thermometer having an optical transmitter in the form of an illumination device and an optical receiver in the form of a light detector.

Preferably, illumination device is understood to be at least one light source/exciting light source and, alternatively, additionally other optical components such as a light tunnel that includes light wave guides/mirrors/lenses/reflecting inner walls/scattering media and the like. Further preferred, light source is understood to be a white light source/an LED (in the VIS and/or IR and/or UV range), a deuterium lamp (UV range) and/or a halogen lamp (VIS range). In other words, the light can be produced at/in/on the instrument branch at the place of radiation/at the at least one inlet opening directly by means of a light source or by the light being guided from a light source by means of light wave guides/mirrors/lenses/light tunnels/scattering media and the like to a place of radiation/a light inlet opening/a light entrance opening of the contact surface of the instrument branch which is provided and adapted to contact the tissue. Further preferred, the light of the illumination device is radiated at a particular angle relative to the tissue contact surface of the respective instrument branch or electrode, i.e., the illumination device has an angled/inclined outlet opening and/or light radiation in/at/on the instrument branch. In yet other words, the light source itself is arranged obliquely/angled on/at/in the instrument branch or has an oblique/angled surface with respect to the tissue contact surface or light emission surface. As an alternative, an optical element such as a mirror and/or a light wave guide can be arranged obliquely on/at/in the contact surface (the surface that is provided and adapted to get in contact with tissue) of the instrument branch and can guide the light from the light source to the place of radiation or the contact surface.

A white light source, viz. a light source that emits the electromagnetic radiation over the entire VIS range, offers the advantage that more information can be obtained from the tissue to be illuminated, thus making a tissue recognition and/or a multivariant data analysis possible. Moreover, there is the option to carry out a plurality of different measurements. For example, at least one illumination device with a white light source and at least one detector may be arranged on the instrument branch which detector is provided and adapted to measure spectral ranges, preferably by different sensors (Si, InGaAs sensors, etc.).

A light source with small spectral bandwidth offers the advantage that the implementation is simple, that such a light source is inexpensive, that such a light source enables a high scanning within a time period to be achieved, and that spaces of more than 2 mm from each other and/or from a detector are possible, as a higher intensity on a particular spectral range is possible.

Preferably, detector or light detector is understood to be at least one sensor/one photodiode and/or one photomultiplier (PMT) and, where necessary, other optical components, such as a light tunnel which may include light wave guides/mirrors/lenses/reflecting inner walls/scattering media and the like. In other words, the light can be measured by the detector/detector part installed in/at/on the instrument branch at the place of diffuse reflection directly by means of a sensor of the detector arranged there or the like at/in/on the instrument branch, or can be guided via a light tunnel which may include light wave guides/mirrors/lenses/reflecting inner walls/scattering media and the like from the contact surface/a light inlet opening of the instrument branch to a sensor or the like arranged distant from the contact surface of the instrument branch or even distant from the instrument branch. Further preferred, the radiation of the light is carried out starting from the illumination device at a particular angle ($0° < \text{angle} \leq 90°$) relative to the tissue contact surface of the respective instrument branch or electrode. Further preferred, the detector includes in/at/on the instrument branch an inlet opening equally angled/tilted relative to the contact surface. In yet other words, the detector is itself arranged obliquely/angled on/at/in the instrument branch or has an oblique/angled surface with respect to the tissue contact surface. Alternatively, an optical element, such as a mirror and/or a light wave guide, can be arranged obliquely on/at/in the contact surface (the surface that is provided and adapted to get in contact with tissue) of the instrument branch and can guide diffuse reflection light to a distant sensor or the like. The light remitted from the body tissue after radiation is preferably spectrally resolved into at least two channels (by means of spectrometers, prisms or different filters) and is then detected by the at least two sensors or the like which, in response hereto, send at least two signals to the computing unit/CPU which transforms the at least two signals into a temperature value.

The electrode for sealing tissue is preferably made of metal, conductive ceramics, metallized ceramics, graphite or metallized graphite. The electrode is further preferably formed to have a surface that is provided and adapted to reflect electromagnetic radiation.

The computing unit preferably comprises a processor and a storage medium. The storage medium is provided and adapted to store steps for carrying out the measurement of the temperature and/or the control and/or regulation of the current of the electrode.

The computing unit controls the illumination device/light source of the illumination device (duration, intensity, wavelength, etc.) by means of a first electrical signal, and the detector detects the light scattered/reflected (exclusively) by the body tissue or the diffuse reflection directly at the tissue to be measured/treated (between the instrument branches) and sends the established data as a second electric signal to the computing unit. The computing unit now calculates, by means of an algorithm on the storage medium, the temperature of the tissue which can be derived from the respective second electrical signal. On the basis of the temperature of the tissue calculated in this way, it is calculated online/real-time which current intensity, which voltage and/or which frequency the electric current that is applied to the at least one electrode is to have.

In addition, in one embodiment, also the resistance of the tissue (tissue impedance) can be established by the computing unit and can be included in the calculation. In other words, the tissue impedance of the tissue at/between the electrodes/sonotrodes can be established so that the current intensity, the voltage and/or the frequency of the electric current applied to the electrode(s) or the ultrasonic converter can be controlled or regulated by the computing unit in response to the established tissue impedance and (in combination with) the second signal of the (optical) temperature measuring device.

Preferably, the computing unit is in connection with the (optical) temperature measuring device according to the invention such that the current intensity, the voltage and/or the frequency of the electric current applied to the at least one electrode can be changed, preferably automatically and/or by a predetermined algorithm, in response to the temperature calculated by the computing unit/CPU.

Preferably, the second electrical signal from the detector corresponds to a light spectrum that represents the wavelength and the intensity of the light detected at the detector. Based on said spectrum, the shift of the spectral absorption maximum of water is calculated/established. On the basis of this shift of the absorption maximum which amounts to about 0.5 nm/K, the temperature can be determined. Since the absorption spectrum of water is characteristic, the shift can be established even without reference measurement and/or with reference measurement.

Preferably, the computing unit is configured such that it comprises at least one of the following steps, or on a storage medium in the computing unit at least one of the following steps in stored (preferably in the following order):

- activating the illumination device by the computing unit with a first electric signal, preferably with an electric current of a particular current intensity and/or a particular voltage and/or a particular frequency,
- emitting an electromagnetic radiation of the illumination device (preferably white light) into the tissue in a particular area in direct vicinity to an electrode or between two opposite electrodes,
- measuring (by means of the detector) the diffuse reflection/the diffuse reflection of the electromagnetic radiation starting from the body tissue,
- sending the measuring results from the detector to the computing unit by means of a second electric signal,
- transforming the second electric signal into a tissue temperature value,
- preferably establishing the tissue impedance, preferably between two electrodes, and
- processing the tissue temperature value and preferably the established tissue impedance by means of the computing unit, preferably by means of a pre-programmed algorithm on the storage medium, for determining a new current intensity, voltage and/or frequency for the electric current applied to the electrode(s) to reach or approach a temperature of the tissue of more than 95° C. and preferably at the same time of less than 100° C.

In one embodiment, the light tunnel that is communicated with the light source can be fed at least at one end by at least one light source, and the at least one other end can end in the instrument branch. In other words, light can be directed from at least one light source via a light wave guide or the like to at least one output which is provided at/on/in the instrument branch. Alternatively, at least one light source, such as the LED, can be located/arranged directly on/at/in the instrument branch.

In one embodiment, the light tunnel that is connected to the detector can have at least one sensor at least at one end and at the at least one other end can end in the instrument branch. In other words, light/diffuse reflection can be directed from at least one input located on/in the instrument branch via a reflecting light channel/a light wave guide or the like to at least one sensor/one photodiode/one photomultiplier or the like. As an alternative, at least one sensor/photodiode/photomultiplier may be located/arranged on/at/in the instrument branch.

Preferably, the illumination device and the detector can share one end of a light tunnel. In other words, the path of rays of the light source and the path of rays of the sensor/photodiode/photomultiplier can share a light tunnel so that both is in optical contact with the body tissue via one single optical opening which simultaneously forms the input and the output of the light on/at/in the instrument branch.

Preferably, a plurality of detectors and a plurality of illumination devices are arranged on at least one instrument branch. The detectors and, resp., illumination devices may be arranged on one instrument branch in a predetermined pattern. The pattern is preferably linear. Alternatively, at least one detector and/or one illumination device can be arranged on a first instrument branch and at least one detector and/or one illumination device can be arranged on a second instrument branch, preferably on sides of opposite instrument branches facing each other. In other words, in this embodiment for bipolar instruments the light can be introduced from an illumination device into the tissue and on an opposite side a detector can measure the light remitted by the tissue.

Preferably, the distance between the at least one illumination device and the at least one detector ranges from 0 to 5 mm, especially preferred from 0 to 1 mm, as there the intensity of the diffuse reflection is very high.

Preferably, the at least one instrument branch includes plural detectors for each illumination device, especially preferred the detectors are arranged at equal and/or different spaces from the illumination device. In other words, the space of an illumination device from a second detector may be larger than the space from a first detector.

Preferably, the illumination device includes a discrete light source, preferably having a defined bandwidth, especially preferred having a bandwidth of less than 100 nm.

Preferably, the (optical) temperature measuring device is arranged on a plane of the instrument branch that is lower than the contact surface of the electrode. In other words, a contact surface of the electrodes and/or of the instrument branches getting in contact with the tissue forms a plane. Said plane is higher in the direction of contact (closer to the tissue) than the plane on which the at least one illumination device and/or the at least one detector is arranged.

Preferably, the (optical) temperature measuring device allows an online/real-time determination of the temperature during a sealing operation/sealing. The online determination is of particular importance to the quality of the sealing. Accordingly, the measurement represents the temperature in the tissue/the tissue temperature and shows no latency period or any falsification of the measured temperature by the thermal capacity of the measuring device, such as by the thermal capacity of electrodes made of metal. It is the advantage of an optical temperature measurement which is sensitive to the water in the held/contacted tissue that said temperature measuring device exhibits no significant thermal capacity.

Preferably, the measurement of diffuse reflection in the instrument branch or in the jaw part of a seal and cut instrument can be carried out independently of the position at which the tissue gets in contact with the instrument branch. In other words, the temperature measuring device is arranged distributed, preferably evenly distributed, on the surface of the instrument branch in the area that is provided and adapted to get in contact with the tissue. As explained above, the at least one instrument branch may include a plurality of exciting and detection paths/illumination or detection paths, preferably along and/or in an electrode.

As afore-stated, in addition or as an alternative to the measurement of the impedance, the temperature is to be measured. The temperature is measured directly in the tissue to be fused preferably between two opposite instrument branches, namely preferably in the (time) course of supply of current to/heating of the tissue. In this way, the change of the state of the tissue can be detected directly/online and thus also reacted to. By extending the algorithm by another control/regulating parameter, it is possible to better evaluate the energy input into the tissue and, thus, to better control/ regulate the fusion of the tissue. In addition, also other characteristics of the tissue, such as the water content in the tissue, can be measured by the temperature measuring device according to the invention.

Preferably, the electrode has at least a first electrode surface on the surface that is provided and adapted to get in contact with the tissue. The electrode is preferably located on an instrument branch body (in the jaw part) of an instrument branch or is formed by the instrument branch. Preferably at least one light source/at least one light guide/at least one optical component (dichroitic mirror/beam splitter/mirror) and/or at least one light detector (or a part thereof) having at least one sensor and possibly one light guide is/are introduced into the electrode and/or the instrument branch. Also, a photodiode or a photomultiplier can be understood to be a sensor. The electrode preferably has at least one light outlet opening from/through which the light of the light source radiates out of the electrode surface and/or into the tissue. The electrode preferably has at least one light inlet opening through which the light radiates/is remitted/reflected (exclusively) from the tissue (diffuse reflection) in/through the electrode surface into the sensor. The electrode preferably has at least one channel provided and adapted to direct data via at least one cable/wiring to at least one computing unit or to direct light via at least one scattering medium/at least one light wave guide/at least one reflecting surface to a remote sensor which, in turn, directs data via at least one cable/wiring to at least one computing unit. When the invention has more than one electrode surface or more than one instrument branch, the electrode surfaces/instrument branches are spaced apart from each other, preferably in parallel. The space between the electrode surfaces/instrument branches is preferably provided and adapted to receive a cutting device such as a knife, scalpel, HF scalpel or the like to be insertable, said cutting device being provided and adapted to sever/cut tissue. Hence, on the at least two sides of the cut of the tissue, the electrode/branch surfaces are formed to coagulate the tissue by means of HF technology.

A narrow-band filter is preferably disposed ahead of the sensor. A light tunnel may be formed in the electrode and/or the instrument branch. In other words, the light tunnel can guide light through the instrument branch and/or the at least one electrode. All embodiments may be adapted to be combined with one another.

In the following, the invention shall be illustrated in detail by means of preferred embodiments with reference to the accompanying drawings.

DETAILED DESCRIPTION

Figure 1:
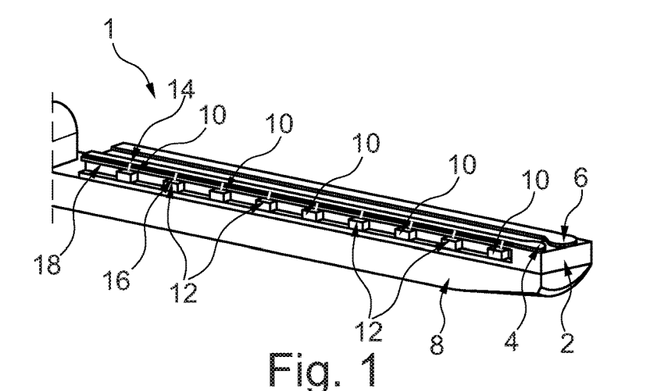
FIG. 1 shows a region of an instrument branch according to a first embodiment.

FIG. 1 illustrates a region of an instrument branch 1 according to a first embodiment. The instrument branch 1 comprises at least one electrode 2 embedded in the instrument branch 1 in an insulated manner. The electrode 2 has, on the branch side provided and adapted to get in contact with a body tissue, a first electrode surface 4 and a second electrode surface 6. The electrode(s) 2 is/are located in particular in/on an instrument branch body 8 of the instrument branch 1 which constitutes one half of an actuatable instrument jaw part. Light sources (LEDs) 10 and light detectors or sensors 12 are alternately introduced into the electrode 2 or into the instrument branch 1/instrument branch body 8. The electrode 2 or the instrument branch 1/instrument branch body 8 includes light outlet openings 14 through which the light of the light source 10 radiates out of the electrode surface 4 and/or 6 or the branch contact surface into the tissue. The electrode 2 or the instrument branch 1/instrument branch body 8 further includes light inlet openings 16 through which the light is remitted from the tissue in/through the electrode surface 4 and/or 6 or through the branch contact surface into the sensor 12. The electrode 2 or the instrument branch 1/instrument branch body 8 includes at least one (longitudinal) channel 18 provided and adapted to direct data/signals from the sensors 12 via a cable (not shown in detail) to a computing unit (not shown in detail).

Figure 2:
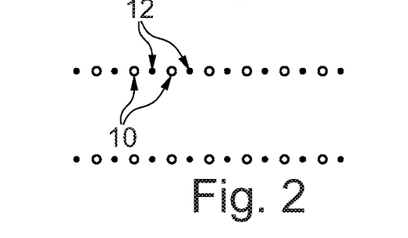
FIG. 2 shows a first illumination and detection arrangement of an instrument branch.

FIG. 2 illustrates a first variant of an illumination and detection arrangement of the instrument branch 1. Each of the embodiments of this application may comprise the first illumination and detection arrangement. The upper row of the illumination and detection arrangement of FIG. 2 is arranged/embedded on/in the second electrode/branch surface 6 of FIG. 1. The lower row of the illumination and detection arrangement of FIG. 2 is arranged/embedded on/in the first electrode/branch surface 4 of FIG. 1. In each of the rows a detector/sensor 12 and an illumination device/light source 12 are alternately arranged. The dark spots represent a detector/sensor 12 and the bright spots represent an illumination device/light source 10. Ahead of the detector/sensor 12, preferably a narrowband (light) filter (not shown) is arranged. Further preferred, the optoelectronic components (sensor 12 and illumination device 10) are disposed on a printed circuit board beneath the electrode/beneath the tissue contact surface of the branch.

Figure 3:
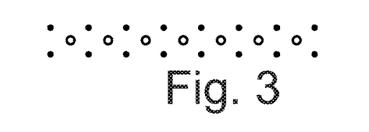
FIG. 3 shows a second illumination and detection arrangement of an instrument branch.

FIG. 3 shows a second variant of an illumination and detection arrangement of an instrument branch. Each of the embodiments of the present application may comprise the second variant of an illumination and detection arrangement. The dark spots represent a sensor 12 and the bright spots represent a light source 10. The second variant of an illumination and detection arrangement is configured so that four sensors 12 are arranged around one light source 10 at an equal distance from the light source 10, the one light source 10 sharing two sensors 12 with another, immediately adjacent light source. The/each light source 10 is located, in other words, in the center of an imaginary rectangle at the corners of which the sensors 12 are positioned.

Figure 4:
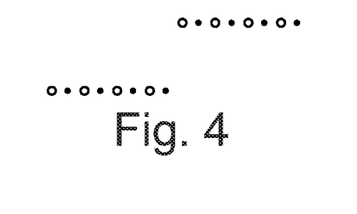
FIG. 4 shows a third illumination and detection arrangement of an instrument branch.

FIG. 4 illustrates a third variant of an illumination and detection arrangement of an instrument branch. Each of the embodiments of this application may comprise the third variant of an illumination and detection arrangement. The dark spots represent a sensor 12 and the bright spots represent a light source 10. The third variant of an illumination and detection arrangement is equal to the first variant of an illumination and detection arrangement, the difference being that the row of the illumination and detection arrangement of the second electrode/branch surface starts where the row of the illumination and detection arrangement of the first electrode/branch surface ends.

Figures 5, 6:
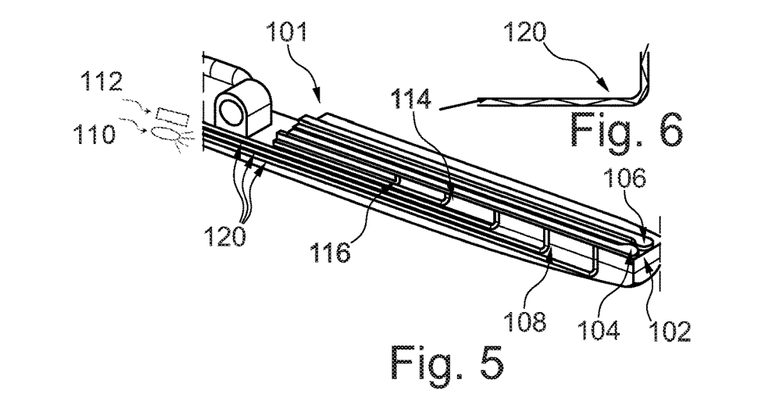
FIG. 5 shows a region of an instrument branch according to a second embodiment.
FIG. 6 shows the guiding of light in the region of the instrument branch according to the second embodiment.

FIG. 5 illustrates a region of an instrument branch 101 according to a second embodiment. The instrument branch 101 includes an electrode 102. The electrode 102 has a first electrode surface 104 and a second electrode surface 106 on the (branch) surface provided and adapted to get in contact with the tissue. In this respect, the branch of the second embodiment corresponds to the branch of the first embodiment. The electrode 102 is located in particular on a distal instrument branch body 108 of the instrument branch 101 which is part of an instrument jaw part. Light sources 110 and sensors 112 (not shown in detail) are introduced into the instrument branch 101, such as in an actuating portion or in a handle portion of the instrument branch 101, distant from the tissue contact surface of the instrument branch body 108. The electrode 102/instrument branch body 108 includes light outlet openings 114 through which the light of the light source is directed and from which light out of the electrode surface 104 and/or 106 or tissue contact surface of the instrument branch body 108 radiates/enters into the tissue. The electrode 102/instrument branch body 108 includes light inlet openings 116 through which the light from the tissue radiates/enters in/through the electrode surface 104 and/or 106 or tissue contact surface of the instrument branch body 108 into a light tunnel 120 which ends in the sensor.

Also, the light from the light source to the light outlet opening 114 is directed through a, preferably different, light tunnel 120. The light tunnels 120 are filled with air or any other gas or have a vacuum. The light tunnels 120 pass through the instrument branch body 108 and/or through the electrode 102. The preferably cylindrical light tunnels 120 have an inner tunnel surface (in the hollow-cylindrical shape) which, in turn, has reflecting characteristics for electromagnetic waves (light waves). The tunnel surface on the inner face of the tunnel is thus provided and adapted to enable total reflection.

FIG. 6 illustrates the guiding of light in the region of the instrument branch/instrument branch body according to the second embodiment in the light tunnel 120. The entering light coming from the light source is totally reflected by the inner surface of the light tunnel 120 and can thus be guided through the light tunnel 120. The total reflection by the inner face of the light tunnel 120 allows the light to be guided even through bent areas/at least a curve or the like. In this case, the light tunnel 120 is guided along the branch body 108 to then arrive, in a curve of substantially 90°, at the tissue contact surface of the branch body 108 (or at any other angle relative to the tissue contact surface) where the light tunnel 120 opens.

Figures 7, 8:
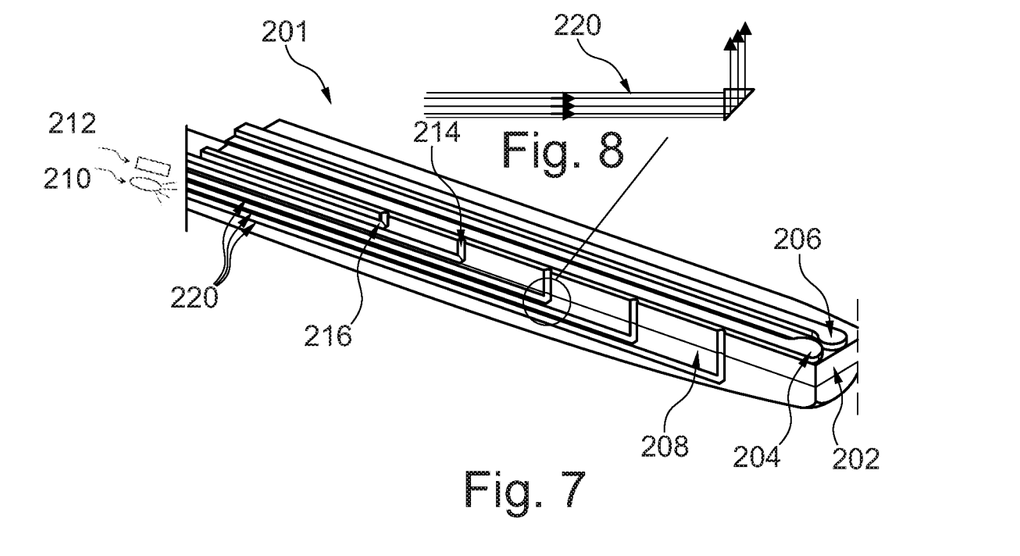
FIG. 7 shows a region of an instrument branch according to a third embodiment.
FIG. 8 shows the guiding of light in the region of the instrument branch according to the third embodiment.

FIG. 7 illustrates a region of an instrument branch 201 according to a third embodiment. The instrument branch 201 includes an instrument branch body 208 forming part of an instrument jaw part which is an electrode or in which an electrode 202 is embedded in an insulating manner, as shown in FIG. 7. The electrode 202 has a first electrode surface 204 and a second electrode surface 206 on the branch surface that is provided and adapted to get in contact with the tissue. The electrode 202 is therefore located on/in the instrument branch body 208 of the instrument branch 201. Light sources 210 and sensors 212 are introduced, at a distance from the tissue contact surface, into the instrument branch 201, such as in an actuating portion or in a handle portion of the instrument branch 201. The electrode 202 or the instrument branch body 208 includes light outlet openings 214 through which the light of the light source is directed and from which light from the electrode surface 204 and/or 206 or the tissue contact surface radiates/enters into the tissue. The electrode 202 or the instrument branch body 208 includes light input openings 216 through which the light radiates/enters from the tissue in/through the electrode surface 204 and/or 206 or the tissue contact surface of the instrument branch body 208 into a light tunnel 220 that ends in a sensor. Also, the light from the light source to the light inlet opening 216 is directed through a, preferably different, light tunnel 220. The light tunnels 220 are filled with air or any other gas or have a vacuum. The light tunnels 220 pass through the instrument branch body 208 and/or through the electrode 202. The light of the light source is introduced/radiated perpendicularly to the opening of the, preferably cylindrical, light tunnel 220/to the longitudinal direction of the cylindrical light tunnel 220. Thus, the light is guided straightly/linearly in the light tunnel 220. For directing the light, at least one mirror and/or one prism is used in the light tunnel 220 to deflect/guide the light at a desired angle. The tunnel 220 may take any geometric shape such as cylindrical, cuboidal, etc.

FIG. 8 illustrates the guiding of light in the region of the instrument branch according to the third embodiment in the light tunnel 220. The entering light coming from the light source is fed linearly/directed/directed in parallel into the light tunnel 220. The guiding by means of at least one mirror in the light tunnel 220 helps guide the light even through angled areas/angles or the like.

Figures 9, 10:
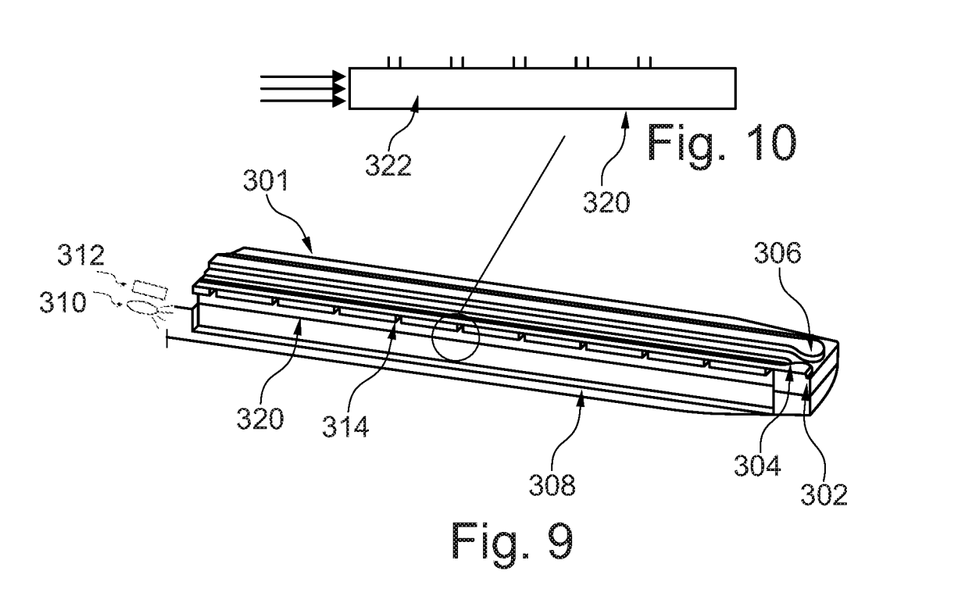
FIG. 9 shows a region of an instrument branch according to a fourth embodiment.
FIG. 10 shows the guiding of light in the region of the instrument branch according to the fourth embodiment.

FIG. 9 illustrates a region of an instrument branch 301 according to a fourth embodiment. The instrument branch 301 comprises an electrode 302 received in an instrument branch body 308 that forms a tissue contact surface. The electrode 302 has a first electrode surface 304 and a second electrode surface 306 on the surface that is provided and adapted to get in contact with the tissue. The electrode 302 is thus located in/on the instrument branch body 308 of the instrument branch 301. Light sources 310 and sensors 312 (not shown in detail) are introduced into the instrument branch 301, such as in an actuating portion or in a handle portion of the instrument branch 301, at a distance from the tissue contact surface of the instrument branch body 308. The electrode 302 or the instrument branch body 308 includes light outlet openings 314 through which the light of the light source is guided and from which light radiates/enters from the electrode surface 304 and/or 306 or the instrument branch body 308 into the tissue. The electrode 302 or the instrument branch body 308 includes light inlet openings 316 (not shown in detail) through which the light radiates/enters from the tissue in/through the electrode surface 304 and/or 306 or through the contact surface of the instrument branch body 308 into a light tunnel 320 that ends in a sensor. Also, the light from the light source to the light outlet opening 314 is directed through a, preferably different, light tunnel (not shown). The light tunnels 320 are filled with scattering bulk material 322. The light tunnels 320 pass through the instrument branch body 308 and/or through the electrode 302. In this embodiment, at least two light tunnels 320 are arranged in parallel in the electrode 302 and/or the instrument branch body 308 in a row/line so that one row with light inlet openings 314 and light outlet openings (not shown) is introduced into each electrode surface 304 and 306. In an embodiment that is not shown, the bulk material of the fourth embodiment can itself be a light source, i.e., the bulk material can be luminous.

FIG. 10 illustrates the guiding of light in the region of the instrument branch according to a fourth embodiment in a light tunnel 320. The entering light coming from the light source is fed into the light tunnel 320, more exactly into the scattering and/or luminous bulk material 322 in the light tunnel 320. By the scattering of the light in the bulk material 322, the light is radiated into the tissue and the remitted light is directed/scattered by a different light tunnel (not shown) having the same structure to the sensor.

Figure 11:
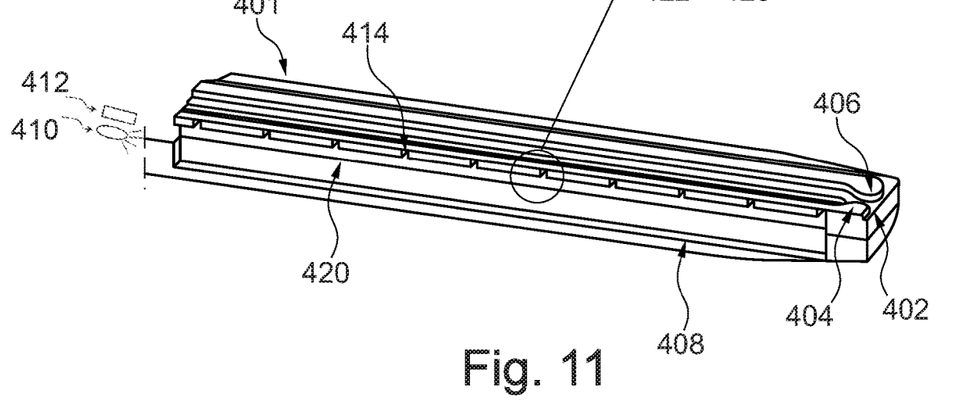
FIG. 11 shows a region of an instrument branch according to a fifth embodiment.

FIG. 11 illustrates a region of an instrument branch 401 according to a fifth embodiment. The instrument branch 401 comprises an electrode 402 which in the present case is embedded in an instrument branch body 408 in an insulating manner. The electrode 402 has a first electrode surface 404 and a second electrode surface 406 on the surface of the instrument branch body 408 which is provided and adapted to get in contact with the tissue. Thus, the electrode 402 is located in/on the instrument branch body 408 of the instrument branch 401. Light sources 410 and sensors 412 are introduced into the instrument branch 401, such as in an actuating portion or in a handle portion of the instrument branch 401, at a distance from the tissue contact surface of the instrument branch body 408 (not shown). The electrode 402 or the instrument branch body 408 includes light outlet openings 414 through which the light of a light source is directed and out of which light radiates/enters from the electrode surface 404 and/or 406 or from the tissue contact surface into the tissue. The electrode 402 or the instrument branch body 408 includes light inlet openings (not shown) through which the light from the tissue radiates/emits in/through the electrode surface 404 and/or 406 or through the tissue contact surface into a light tunnel 420 that ends in a sensor. Also, the light from the light source to the light outlet opening 414 is directed through a, preferably different, light tunnel (not shown). The light tunnels 420 are filled with a structured bulk material 422. The light tunnels 420 pass through the instrument branch body 408 and/or through the electrode 402. In this embodiment, at least two light tunnels 420 are arranged in parallel in the electrode 402 and/or the instrument branch body 408 in a row/line so that one row with light inlet openings 414 and light outlet openings (not shown) is introduced into each electrode surface 404 and 406. In an embodiment that is not shown, the bulk material of the fifth embodiment may itself be a light source, i.e., the bulk material can be luminous.

Figure 12:
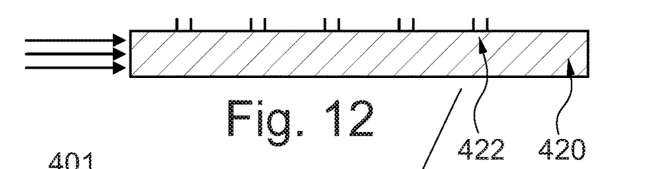
FIG. 12 shows the guiding of light in the region of the instrument branch according to the fifth embodiment.

FIG. 12 illustrates the guiding of light in the region of the instrument branch according to the fifth embodiment in a light tunnel 420. The entering light coming from the light source is fed into the light tunnel 420, more precisely into the structured bulk material 422 inside the light tunnel 420. The structure of the insert in the bulk material 422 causes the light to be radiated into the tissue and the remitted light is directed/scattered to a sensor by a different light tunnel (not shown) of the same structure.

Figure 13:
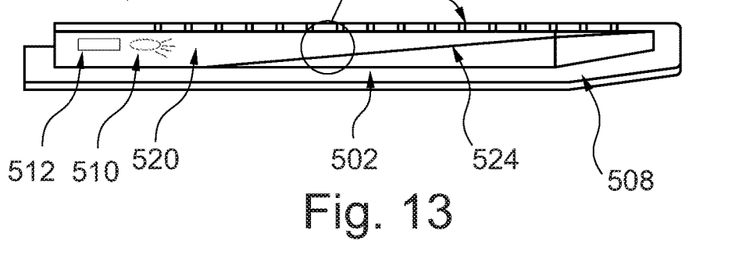
FIG. 13 shows a region of an instrument branch according to a sixth embodiment.

FIG. 13 illustrates a region of an instrument branch 501 according to a sixth embodiment. The instrument branch 501 comprises an electrode 502, wherein, in this embodiment, the instrument branch body 501 and the electrode 502 correspond, as regards their structure and arrangement, to the preceding embodiments. In the instrument branch body 508, light sources 510 and sensors 512 are introduced (not shown in detail). The electrode 502/instrument branch body includes light outlet openings 514 through which the light of a light source is directed and from which light radiates/enters into the tissue. The electrode 502/instrument branch body includes light inlet openings (not shown) through which the light radiates/enters from the tissue into a light tunnel 520 that ends in a sensor. The light from the light source to the light inlet opening 514 is directed through at least one light tunnel 520. In this embodiment, one single light tunnel 520 is formed in the electrode 502 and, thus, in the instrument branch body 501. One row with light outlet openings 514 and light inlet openings (not shown) is introduced into the electrode 502 or in the instrument branch body. At least one silvered/reflecting oblique/angled plane 524 is formed in the light tunnel 520. The plane 524 can be manufactured by polishing the electrode or the instrument branch body or by introducing a mirror into the light tunnel 520. The light tunnel 520 passes through the instrument branch body. At least one row with light outlet openings 514 and light inlet openings (not shown) is introduced into a surface of the electrode 502/instrument branch body. Alternatively, or additionally, one single light tunnel 520 of this type can serve both for exciting and for receiving reflected light—with the appropriate filters. This means that behind the light source a filter corresponding to the diffuse reflection wavelength range is disposed, but the remaining light is guided into the tissue and is received by the same and/or an adjacent opening and is returned to the sensor via the same reflecting plane 524.

Figure 14:
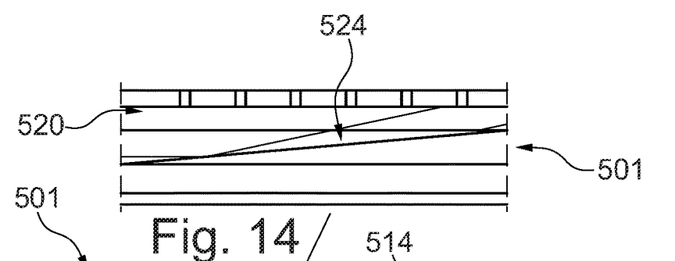
FIG. 14 shows the guiding of light in the region of the instrument branch according to the sixth embodiment.

FIG. 14 illustrates the guiding of light in the region of the instrument branch 501 according to the sixth embodiment in the light tunnel 520. The entering light coming from the light source is fed into the light tunnel 520 and is deflected by the angled reflecting plane 524 at a predetermined angle (preferably at an angle ranging from 0° to 90°). The light is radiated into the tissue by the mirror(s)/reflecting surface/reflecting plane 524, and the remitted light is directed/guided to a sensor by a different light tunnel (not shown) of the same structure.

Figures 15, 16:
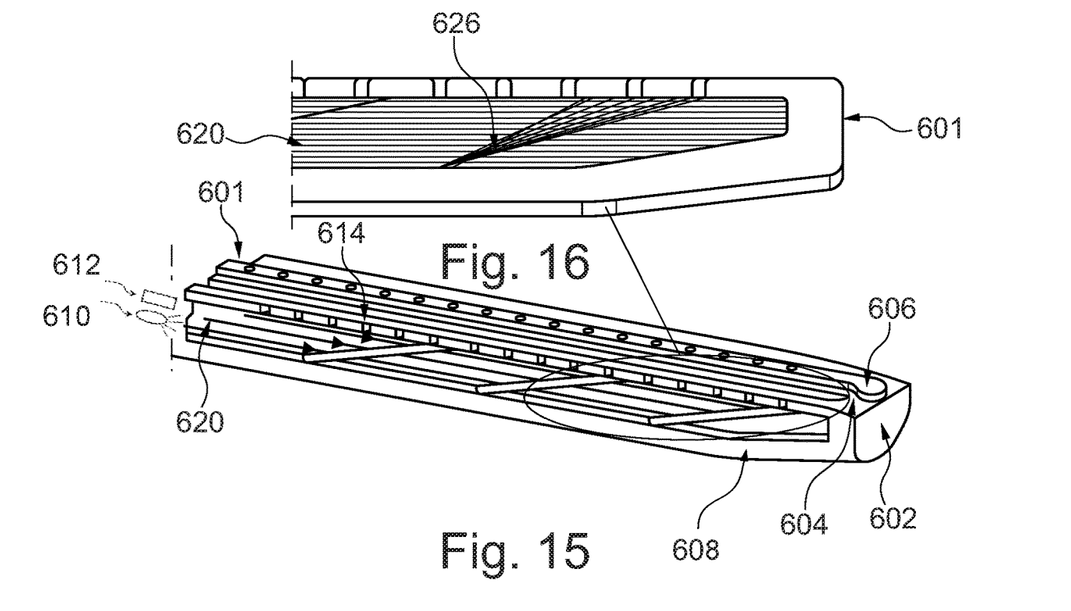
FIG. 15 shows a region of an instrument branch according to a seventh embodiment.
FIG. 16 shows the guiding of light in the region of the instrument branch according to the sixth embodiment.

FIG. 15 illustrates a region of an instrument branch 601 according to a seventh embodiment. The instrument branch 601 comprises an electrode 602 received by an instrument branch body 608. The electrode 602 has a first electrode surface 604 and a second electrode surface 606 on the surface of the instrument branch body 608 that is provided and adapted to get in contact with the tissue. In the instrument branch body 608, light sources 610 and sensors 612 are introduced (not shown in detail). The instrument branch body 608 includes light outlet openings 614 through which the light of a light source (not shown) is guided and radiates/enters from the tissue contact surface into the tissue. The instrument branch body 608 further includes light inlet openings (not shown) through which the light radiates/enters from the tissue in/through the tissue contact surface of the instrument branch body 608 into a light tunnel 620 that ends in a sensor. Also, the light from the light source to the light outlet opening 614 is directed through a second light tunnel (not shown). At least one semi-translucent plane 626 that transmits part of an electromagnetic radiation, viz. is translucent to a part of the light, and reflects a part of the light, is introduced into the light tunnel 620. Preferably, the semi-translucent plane is a semi-translucent mirror and, further preferred, plural semi-translucent planes 626 are arranged in series in the light tunnel.

FIG. 16 illustrates the guiding of light in the region of the instrument branch 601 according to the seventh embodiment in a light tunnel 620. The entering light coming from the light source is fed into the light tunnel 620. The entering light coming from the light source is fed linearly/directed/directed in parallel into the light tunnel 620. The light is guided/reflected/mirrored via angled areas/angles or the like by being guided via at least one semi-translucent mirror 626 in the light tunnel 620. The light which penetrates a semi-translucent mirror 626 is incident on another semi-translucent mirror 626 arranged at the same angle as the preceding mirror, and so forth. The light is radiated into the tissue by the semi-translucent mirror/reflecting surface/reflecting plane 626, and the remitted light is directed/guided to a sensor by a different light tunnel (not shown) of the same structure.

Figures 17, 18:
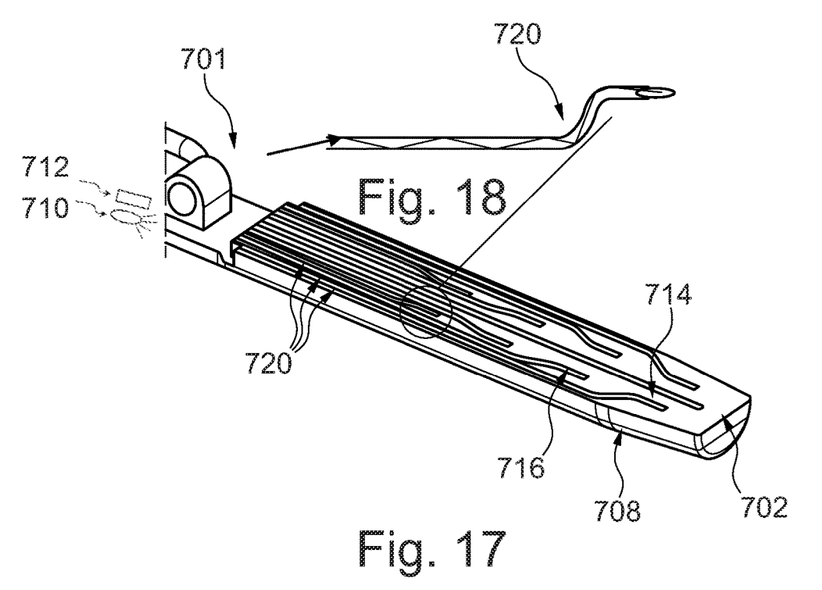
FIG. 17 shows a region of an instrument branch according to an eighth embodiment.
FIG. 18 shows the guiding of light in the region of the instrument branch according to the eighth embodiment.

FIG. 17 illustrates a region of an instrument branch 701 according to an eighth embodiment. The instrument branch 701 comprises an electrode 702. The electrode 702 is located on an instrument branch body 708 of the instrument branch 701. Light sources 710 and sensors 712 are introduced into the instrument branch 701, such as in an actuating portion or in a handle portion of the instrument branch 701, remote from the instrument branch body 708, preferably externally (not shown in detail). The instrument branch body 708 includes at least one light tunnel 720 through which the light of the light source is directed and from which the light radiates/enters into the tissue. The instrument branch body 708 includes at least one further light tunnel 720 through which the light is guided from the tissue to a sensor. In this embodiment, the light tunnels 720 are formed by light wave guides such as glass fibers.

FIG. 18 illustrates the guiding of light in the region of the instrument branch according to the eighth embodiment in a light tunnel 720. The entering light coming from the light source is totally reflected by the inner surface of the light tunnel 720 and, thus, can be directed through the light tunnel 720. The total reflection by the inner face of the light tunnel 720 can help guide the light even through bent areas/at least a curve or the like.

Figures 19, 20:
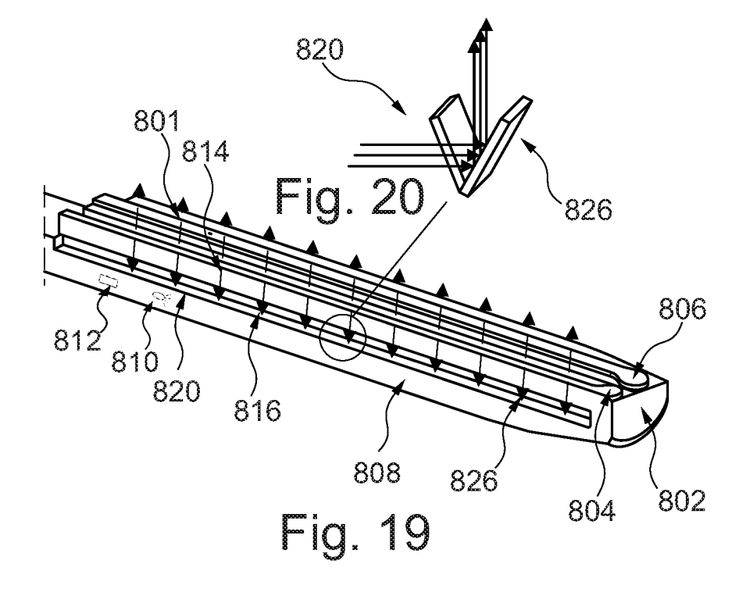
FIG. 19 shows a region of an instrument branch according to a ninth embodiment.
FIG. 20 shows the guiding of light in the region of the instrument branch according to the ninth embodiment.

FIG. 19 illustrates a region of an instrument branch 801 according to a ninth embodiment. The instrument branch 801 comprises an electrode 802. The electrode 802 has a first electrode surface 804 and a second electrode surface 806 on the tissue contact surface of its instrument branch body that is provided and adapted to get in contact with the tissue. Light sources 810 and sensors 812 are introduced into the instrument branch body 808 (not shown in detail). The instrument branch body moreover includes light outlet openings 814 through which the light of a light source is directed and radiates/enters into the tissue. The instrument branch body also includes light inlet openings 816 through which the light radiates/enters from the tissue in/through the instrument branch body into a light tunnel 820 that ends in a sensor. The light from the light source to the light outlet opening 814 is directed through the same light tunnel. In other words, light outlet openings 814 may act as light inlet openings 816, and vice versa. At least two semi-translucent planes 626 which transmit a part of an electromagnetic radiation, viz. are translucent to a part of the light, and reflect a part of the light are introduced into the light tunnel 820. Preferably, the semi-translucent plane is a semi-translucent mirror and, further preferred, plural semi-translucent planes 626 are arranged in series in the light tunnel. This arrangement in this embodiment helps assign one semi-translucent mirror to a light outlet opening 814 or a light inlet opening 816.

FIG. 20 illustrates the guiding of light in the region of the instrument branch 801 according to the ninth embodiment in a light tunnel 820. The entering light coming from the light source is fed into the light tunnel 820. The entering light coming from the light source is fed into the light tunnel 820 linearly/directed/directed in parallel. The light is guided/reflected/mirrored via angled areas/angles or the like by being guided via at least two semi-translucent mirrors 826 in the light tunnel 820. The light penetrating a semi-translucent mirror 826 is incident on at least one further semi-translucent mirror 826 which is arranged at the same angle as the preceding mirror, and so forth. The light is radiated into the tissue by the semi-translucent mirror/reflecting surface/reflecting plane 826, and the remitted light is directed/guided to a sensor by the same light tunnel 820 but through an adjacent opening. In yet other words, an opening at the same time is a light outlet opening and a light inlet opening to an adjacent opening.

Figures 21, 22:
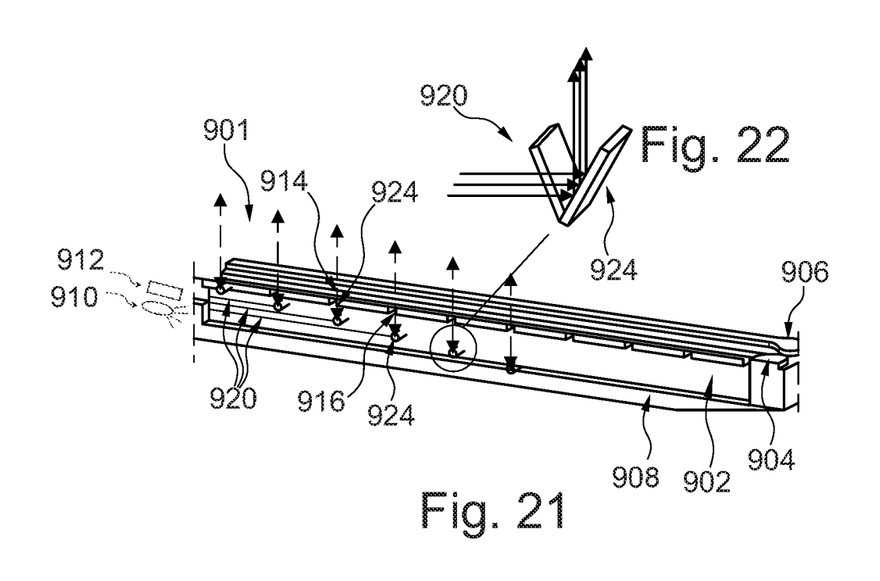
FIG. 21 shows a region of an instrument branch according to a tenth embodiment.
FIG. 22 shows the guiding of light in the region of the instrument branch according to the tenth embodiment.

FIG. 21 illustrates a region of an instrument branch 901 according to a tenth embodiment. The instrument branch 901 comprises an electrode 902, in this embodiment the instrument branch body and the electrode corresponding to the preceding embodiments as regards their structure and arrangement. In the instrument branch, such as in an actuating portion or in a handle portion of the instrument branch 901, light sources 910 and sensors 912 are consequently introduced at a distance from the tissue contact surface of the instrument branch body (not shown in detail). The instrument branch body includes light outlet openings 914 through which the light of a light source that is not shown is directed and from which light radiates/enters into the tissue. The instrument branch body 908 further includes light inlet openings 916 through which the light radiates/emerges from the tissue into a light tunnel 920 that ends in a sensor. The light from the light source to the light outlet opening 914 is directed through at least one light tunnel 920. The light from the light inlet opening 916 to the sensor is directed through at least one further light tunnel 920 (of the same design). In this embodiment, thus at least two light tunnels 920 are formed in the instrument branch body 908. The light outlet opening/s 914 and light inlet opening/s 916 are alternately introduced into the instrument branch body. At least one silvered/reflecting oblique/angled plane 924 is formed in the light tunnel 920.

FIG. 22 illustrates the guiding of light in the region of the instrument branch 901 according to the tenth embodiment in the light tunnel 920. The entering light coming from the light source is fed into the light tunnel 920 and is deflected by the angled reflecting plane 924 at a predetermined angle (preferably at an angle ranging from 0° to 90°). The light is radiated into the tissue by the mirror(s)/reflecting surface/reflecting plane 924, and the remitted light is directed/guided to a sensor by a different light tunnel 920 of the same structure.

Figures 23, 24:
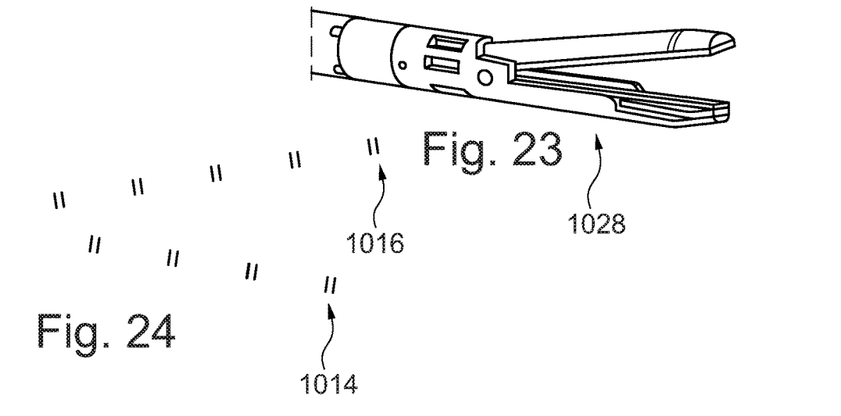
FIG. 23 shows a bipolar instrument branch according to preceding embodiments.
FIG. 24 shows opposite detectors and illumination devices on a bipolar HF instrument.

FIG. 23 illustrates a bipolar instrument branch 1028 according to the foregoing embodiments. The embodiments one to ten are provided and adapted to be used in a bipolar medical HF instrument in which two instrument branch bodies are preferably mounted so as to be pivotable relative to each other and define a tissue receiving gap therebetween.

FIG. 24 illustrates detectors and illumination devices facing each other on a bipolar HF instrument. Accordingly, the light outlet openings 1014 of the illumination devices and the light inlet openings 1016 of the detectors are arranged on respective opposite instrument branches/instrument branch bodies.

Figure 25:
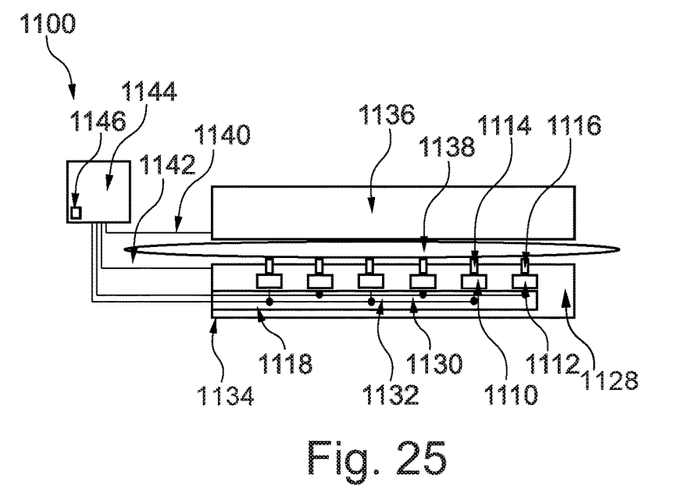
FIG. 25 shows a schematic view of a medical device according to the invention.

FIG. 25 illustrates a schematic view of a medical device 1100 according to the invention. A light source 1110 is provided and adapted to irradiate light. A sensor 1112 is provided and adapted to detect light. The light source radiates the light through a light outlet opening 1114. The sensor 1112 receives light via a light inlet opening 1116. The light sources 1110 and the sensors 1112 are connected to data lines 1130 and 1132 located in a channel 1118. The channel 1118 is formed in an instrument branch body 1128 which also receives the electrodes in an insulating manner. The one instrument branch body in which the electrode 1134 is received clamps the tissue 1138 by an instrument branch body in which the opposite electrode 1136 is received. The electrode 1134 and the electrode 1136 are connected to the lines 1140 and 1142. The data lines 1130 and 1132 as well as the lines 1140 and 1142 are connected to a computing unit 1144 which includes a storage medium 1146.

Figure 26:
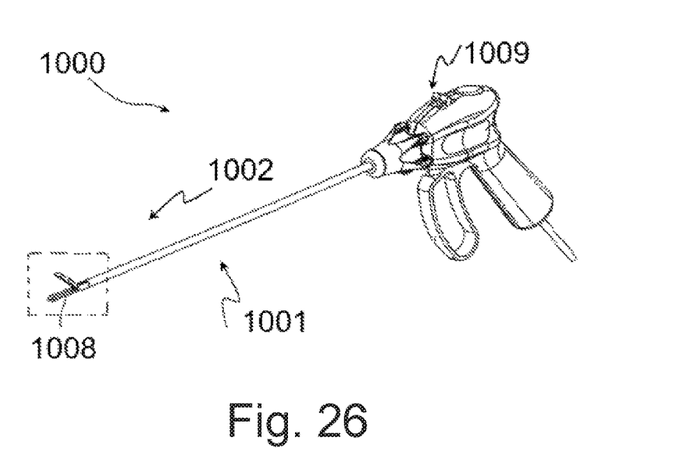
FIG. 26 shows an example of a medical high-frequency surgical instrument according to the invention.

FIG. 26 illustrates an example of a medical high-frequency surgical instrument 1000 according to the invention comprising a first instrument branch 1001 and a second instrument branch 1002. At the distal end of the first instrument branch 1001 an instrument branch body 1008 is formed and at the proximal end of the first instrument branch 1001 an actuating or handle portion 1009 is formed.

The invention claimed is:

1. A method for measuring temperature, comprising the steps of:
    emitting light with an illumination spectrum into tissue from a plurality of illumination devices;
    receiving a diffuse reflection of the light with a diffuse reflection spectrum from the tissue by a plurality of detectors, wherein the plurality of illumination devices and the plurality of detectors are alternatingly formed or arranged in or on one instrument branch and are in electrical connection with a computing unit, or the plurality of illumination devices and the plurality of detectors are alternatingly formed or arranged in or on each of two opposite instrument branches and are in electrical connection with a computing unit;
    converting the diffuse reflection spectrum into a detector signal using the plurality of detectors;
    sending the detector signal to the computing unit;
    evaluating the diffuse reflection spectrum from the detector signal with the computing unit;
    evaluating an absorption spectrum of the tissue by comparing the illumination spectrum to the diffuse reflection spectrum with the computing unit;
    determining at least one absorption maximum from the absorption spectrum with the computing unit; and
    calculating a temperature in the tissue by comparing the at least one absorption maximum to at least one reference with the computing unit.

2. The method according to claim 1, further comprising the step of storing at least one reference in the form of an absorption maximum at a particular temperature in the computing unit.

3. The method according to claim 1, further comprising the step of applying the plurality of illumination devices and the plurality of detectors to the tissue.

4. The method according to claim 1, further comprising the step of controlling and/or regulating and/or switching off a device with the computing unit based on the temperature in the tissue and/or a tissue impedance.

5. The method according to claim 1, wherein the method is carried out during a sealing operation.

6. A medical instrument comprising:
    at least one instrument branch comprising at least one electrode adapted to be supplied with current for sealing and/or cutting tissue, wherein the current is controllable and/or regulated by a computing unit; and
    at least one optical temperature measuring device comprising a plurality of illumination devices and a plurality of detectors, the plurality of illumination devices and the plurality of detectors being alternatingly formed or arranged in or on one of the at least one instrument branch and which are in electrical connection with the computing unit, or the plurality of illumination devices and the plurality of detectors being alternatingly formed or arranged in or on each of two opposite instrument branches of the at least one instrument branch and are in electrical connection with a computing unit, wherein:
        the computing unit is adapted to transform signals from the plurality of detectors into temperature values;
        the plurality of illumination devices are adapted to emit light with an illumination spectrum into the tissue;
        the plurality of detectors are adapted to receive a diffuse reflection of a light emitted with a diffuse reflection spectrum from the tissue, convert the diffuse reflection spectrum into a detector signal, and send the detector signal to the computing unit; and
        the computing unit is adapted to:
            evaluate the diffuse reflection spectrum from the detector signal,
            evaluate an absorption spectrum of the tissue by comparing the illumination spectrum to the diffuse reflection spectrum,
            determine at least one absorption maximum from the absorption spectrum, and
            calculate at least one calculated temperature value in the tissue by comparing the at least one absorption maximum to at least one reference.

7. The medical instrument according to claim 6, wherein the computing unit is connected with the at least one optical temperature measuring device such that a current intensity, a voltage and/or a frequency of an electric current applied to the at least one electrode is variable in response to the at least one calculated temperature value.

8. A medical instrument comprising:
   at least one instrument branch comprising at least one electrode adapted to be supplied with current for sealing and/or cutting tissue, wherein the current is controllable and/or regulated by a computing unit; and
   at least one optical temperature measuring device comprising a plurality of illumination devices and a plurality of detectors, each of the plurality of illumination devices and the plurality of detectors being alternatingly formed or arranged in or on the at least one instrument branch or alternately on two opposite instrument branches and which are in electrical connection with the computing unit, the computing unit adapted to transform signals from the plurality of detectors into temperature values, wherein the plurality of detectors and/or the plurality of illumination devices include(s) at least one light tunnel.

9. The medical instrument according to claim 8, wherein the plurality of illumination devices and the plurality of detectors share an end of the at least one light tunnel.

10. The medical instrument according to claim 8, wherein the at least one light tunnel is filled with a scattering bulk material.

11. The medical instrument according to claim 6, wherein a surface of the at least one electrode is made of a reflecting material.

12. The medical instrument according to claim 6, wherein the plurality of detectors comprises a first detector and a second detector, and wherein one of the plurality of illumination devices is spaced farther from the first detector than from the second detector.

13. The medical instrument according to claim 6, wherein the at least one optical temperature measuring device is arranged on a plane which is lower than a contact surface of the at least one electrode.

14. The medical instrument according to claim 6, wherein the at least one instrument branch comprises a first instrument branch and a second instrument branch, and wherein the first instrument branch comprises the plurality of illumination devices and the second instrument branch comprises the plurality of detectors.

15. The medical instrument according to claim 6, wherein the plurality of illumination devices are arranged obliquely/angled on/at/in the at least one instrument branch or have an oblique/angled surface with respect to a tissue contact surface or light emission surface.

16. The medical instrument according to claim 6, wherein the plurality of detectors are arranged obliquely/angled on/at/in the at least one instrument branch or have an oblique/angled surface with respect to a tissue contact surface.

17. The medical instrument according to claim 6, wherein an optical element is arranged obliquely/angled on/at/in a contact surface of the at least one instrument branch.

* * * * *